United States Patent [19]

Sakamaki et al.

[11] Patent Number: 5,696,492
[45] Date of Patent: Dec. 9, 1997

[54] MEDICAL ALARMING SYSTEM

[75] Inventors: Takanori Sakamaki; Yasuhiro Fukui; Hajime Ysuda, all of Tokyo, Japan

[73] Assignee: Nihon Kohden Corporation, Tokyo, Japan

[21] Appl. No.: 730,480

[22] Filed: Oct. 11, 1996

[30] Foreign Application Priority Data

Oct. 13, 1995 [JP] Japan ................... 7-265431

[51] Int. Cl.$^6$ .................................... G08B 23/00
[52] U.S. Cl. ........................... 340/573; 340/522
[58] Field of Search .................. 340/573, 522; 364/413.02, 413.03; 128/903, 906

[56] References Cited

U.S. PATENT DOCUMENTS

| | | | |
|---|---|---|---|
| 3,924,130 | 12/1975 | Cohen et al. | 340/573 |
| 4,051,522 | 9/1977 | Healy et al. | 128/903 |
| 4,803,625 | 2/1989 | Fu et al. | 364/413.03 |
| 5,437,278 | 8/1995 | Wilk | 364/413.02 |
| 5,534,851 | 7/1996 | Russek | 340/573 |

*Primary Examiner*—Jeffery Hofsass
*Assistant Examiner*—Sihong Huang
*Attorney, Agent, or Firm*—Hoffmann & Baron, LLP

[57] ABSTRACT

A medical alarming system for delivering an alarm in response to any abnormal change arising during the monitoring of a patient's physiological signals, and which causes less stress in the patient from less disturbance to his or her sleep. The system a) evaluates whether a change in the output from a physiological sensor is normal or not, thereby determining the occurrence of abnormal change; b) detects the image of the patient's bedside; c) evaluates whether the current image of the bedside agrees with a predetermined criteria; d) determines the appropriate type of alarm to be actuated; and e) delivers the determined alarm.

4 Claims, 9 Drawing Sheets

FIG. 8

| ALARM SIGNAL | ALARM OUTPUT | SERIOUSNESS | STRESS TO PATIENT |
|---|---|---|---|
| ALARM 0 | NO ALARM | — | LITTLE |
| ALARM 1 | VISUAL ALARM, AUDITORY ALARM (LITTLE VOLUME) | LOW | ↓ |
| ALARM 2 | VISUAL ALARM, AUDITORY ALARM (MEDIUM VOLUME) | MODERATE | |
| ALARM 3 | VISUAL ALARM, AUDITORY ALARM (LARGE VOLUME), PAGER | HIGH | MUCH |

FIG. 9

| PRESENCE / ABSENCE OF ATTENDANT NORMAL / ABNORMAL | NO ATTENDANT | ATTENDANT IS PRESENT |
|---|---|---|
| NORMAL | ALARM 0 | ALARM 0 ATTENDANT IS AT BEDSIDE |
| ABNORMALITY FROM MANIPULATED STOPCOCK | ALARM 3 ABNORMALITY FROM DISORGANIZED MEASURING | ALARM 1 ABNORMALITY FROM DISORGANIZED MEASURING |
| ABNORMALITY FROM OTHER SOURCES THAN STOPCOCK | ALARM 2 ABNORMALITY IN PATIENT'S STATE BUT NO ATTENDANT IS AT BEDSIDE | ALARM 1 ABNORMALITY IN PATIENT'S STATE BUT ATTENDANT IS AT BEDSIDE |

FIG.10

| TIME | t1 | t2 | t3 | t4 | t5 | t6 | t7 | t8 | t9 | t10 |
|---|---|---|---|---|---|---|---|---|---|---|
| EVENT | NONE | NURSE COMES TO BEDSIDE | NURSE PREPARES FOR BLOOD SAMPLING | NURSE MANIPULATES STOPCOCK | NURSE SAMPLES BLOOD | NURSE LEAVES BEDSIDE, LEAVING STOPCOCK DISORGANIZED | NURSE COMES TO BEDSIDE | NURSE PUT STOPCOCK IN ORDER | NURSE LEAVES BEDSIDE | NONE |
| CENTAL VENOUS PRESSURE (CVP) DATA | NORMAL | NORMAL | NORMAL | ABNORMALITY FROM MEASURING MEANS | ABNORMALITY FROM MEASURING MEANS | ABNORMALITY FROM MEASURING MEANS | ABNORMALITY FROM MEASURING MEANS | NORMAL | NORMAL | NORMAL |
| VIDEO DATA | NO ATTENDANT | ATTENDANT IS PRESENT | ATTENDANT IS PRESENT | ATTENDANT IS PRESENT | ATTENDANT IS PRESENT | NO ATTENDANT | ATTENDANT IS PRESENT | ATTENDANT IS PRESENT | NO ATTENDANT | ATTENDANT IS PRESENT |
| ALARM | ALARM 0 | ALARM 0 | ALARM 0 | ALARM 1 | ALARM 1 | ALARM 3 | ALARM 1 | ALARM 0 | ALARM 0 | ALARM 0 |

MEDICAL ALARMING SYSTEM

BACKGROUND OF THE INVENTION

1. Field of the Invention

This invention relates to an alarming system suitable when used in combination with medical equipment in ICUs (intensive care units), wards of the hospital and homes where patients are in beds.

2. Description of the Related Art

Conventionally, when physiological signals of a patient are measured and something abnormal happens about them, an alarm is delivered from an alarming system which has been placed on the bedside of the patient and set to give a predetermined alarm in case such events occur, regardless of whether the attendant is present at the bedside for the treatment, care or help of the patient.

Such an alarm is delivered to inform people engaged in the treatment, care or help of the patient of the occurrence of abnormal events in physiological signals, but to the patient it is a rather nuisance. Therefore, separation of the alarm as far as possible from the patient would be desirable. The alarming system conventionally used, however, delivers the same type of alarm or a sound same in volume regardless of whether the attendant is present at the bedside for the treatment, care or help of the patient. Usually the sound has a volume too big for the patient, because it has been designed to have a sufficient volume to alarm people engaged in the treatment, care or help of the patient who might be apart from the bedside. Thus, the alarm, whenever it is delivered, adds stresses of the patient, makes him/her nervous, and interferes with his/her sound sleep.

SUMMARY OF THE INVENTION

The present invention intends to provide a medical alarming system which gives an alarm whenever something abnormal happens in monitored physiological signals but in a manner not to cause stresses and anxieties in the patient, nor to interfere with his/her sound sleep as much as possible.

To achieve this object, the system of this invention is furnished with the following means: a first evaluating means for evaluating whether the current output from a physiological signal detecting means to check the physiological signals of the patient is normal or not; an image detecting means for detecting the outlook of the bedside; a second evaluating means for evaluating whether the current outlook of the bedside agrees with a predetermined criterion or not; an alarm type determining means for determining, for the case judged to be abnormal by the first evaluating means, the alarm type according to the judgement given by the second evaluating means for the same case, that is, according to the importance of the case in question with respect to the situation around the patient; and an alarm delivering means for delivering an alarm varying in stimulating activity to the patient or the type of alarm that has been determined by the alarm type determining means.

According to the system of this invention, the type of alarm can be varied according to whether the attendant is present around the patient or not; when the attendant is present, the alarm delivered can be set to a low level. Therefore, the system of this invention delivers alarms that cause only minimal stresses and anxieties in the patient, and least interfere with his/her sound sleep.

If abnormalities were detected in signals from the patient, the system of this invention could determine whether the abnormalities are derived from some failure in the measuring means or from the diseased condition of the patient, and, in addition, whether the attendant is present at bedside at that moment, and then it can adjust the type of alarm precisely according to the nature of the abnormalities and to the situation around the patient. Therefore, this system can relieve the patient more effectively from stresses and anxieties caused by alarms, and less interfere with his/her sound sleep.

BRIEF DESCRIPTION OF THE DRAWINGS

FIG. 8 gives a list of the type of alarm and its outputs.

FIG. 9 describes how the type of alarm is determined according to a given situation.

FIG. 10 gives a comparison of abnormal events with alarms delivered in correspondence therewith as an illustration of how the present system operates.

DETAILED DESCRIPTION OF THE PREFERRED EMBODIMENTS

Figure 1:
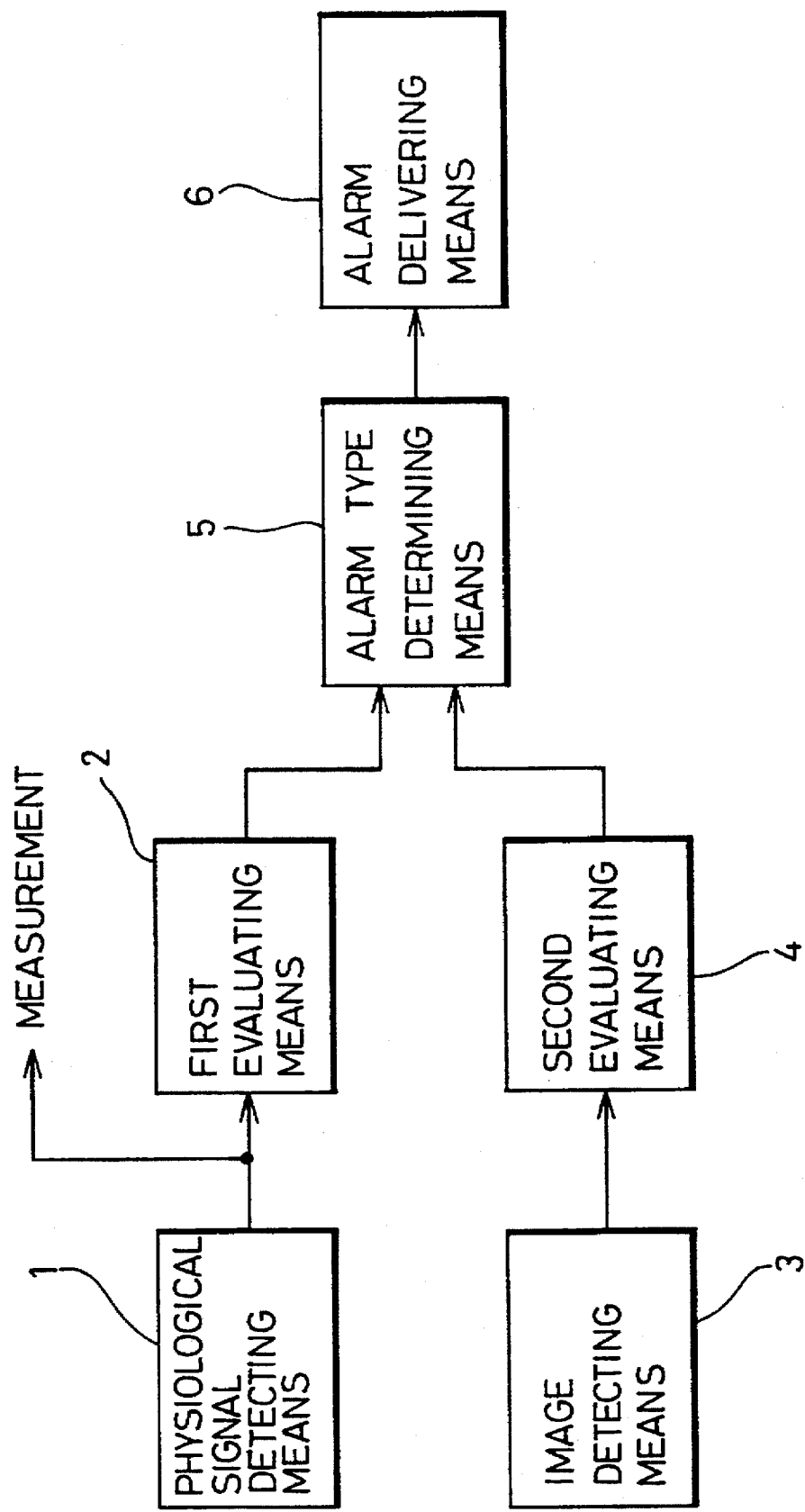
FIG. 1 shows the basic constitution of the present invention.

FIG. 1 shows the basic constitution of the alarming system of this invention. Namely, the present alarming system is provided with: a physiological signal detecting means 1 for detecting physiological signals from the patient lying on bed; a first evaluating means 2 for evaluating whether the current output from the physiological signal detecting means is normal or not; an image detecting means 3 for detecting the outlook of the bedside; a second evaluating means 4 for evaluating whether the current outlook of the bedside agrees with a predetermined criterion or not; an alarm type determining means 5 for determining, for the case judged to be abnormal by the first evaluating means 2, the alarm type according to the judgement given by the second evaluating means 4 for the same case; and an alarm delivering means 6 for delivering the type of alarm that has been determined by the alarm type determining means 5.

The second evaluating means 4 judges whether the current image of the bedside corresponds with a predetermined criterion or not. For example, if an attendant appears at the bedside, a corresponding change arises in the image. If that change corresponds with a predetermined criterion, the means 4 registers the correspondence. If an abnormal event concurrently occurs in physiological signals from the patient, the alarm type determining means 5 determines the type of alarm according to the registered state of the means 4, and thus the alarm delivering means 6 delivers different types of alarm according to whether an attendant is at the bedside or not.

In FIG. 1, the individual means are so designed as to exhibit following functions: if an abnormal event happens, the first evaluating means 2 determines whether the abnormal event arises from the measuring means or from the diseased condition of the patient; the alarm type determining means 5 determines an appropriate type of alarm according to the evaluations given by the first and second evaluating means 2 and 4, that is, the alarm type determining means 5 determines an appropriate type of alarm according to whether the abnormality arises from the measuring means or from the patient, and to whether the attendant is present at the bedside or not; and thus the alarm delivering means 6 delivers an appropriate type of alarm in correspondence with the current combination from among all possible alternatives: the abnormality may come from the measuring means or from the patient, and the attendant may be present or absent at the bedside.

Figure 2:
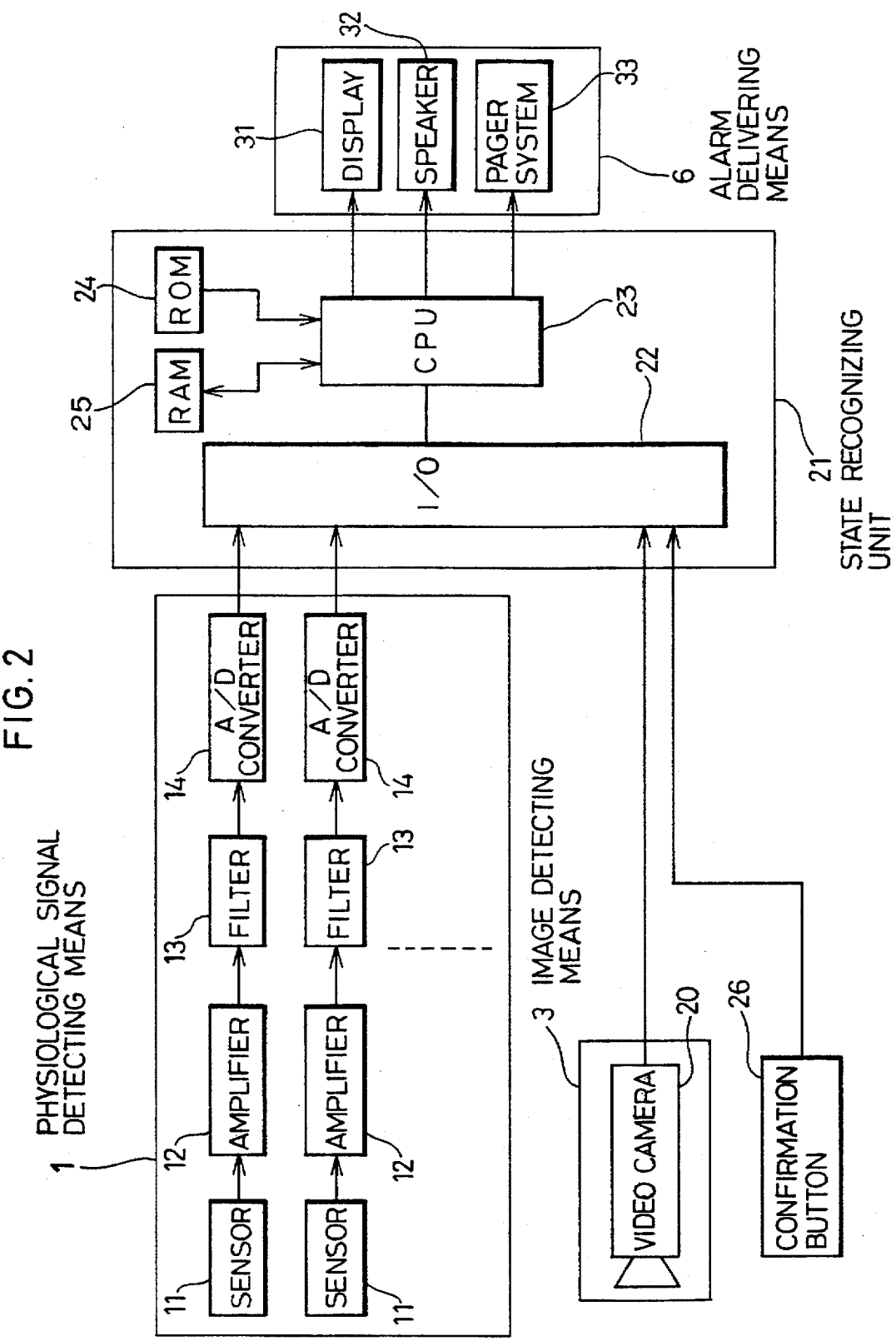
FIG. 2 shows the overall constitution of the system which is put to use.
Figure 3:
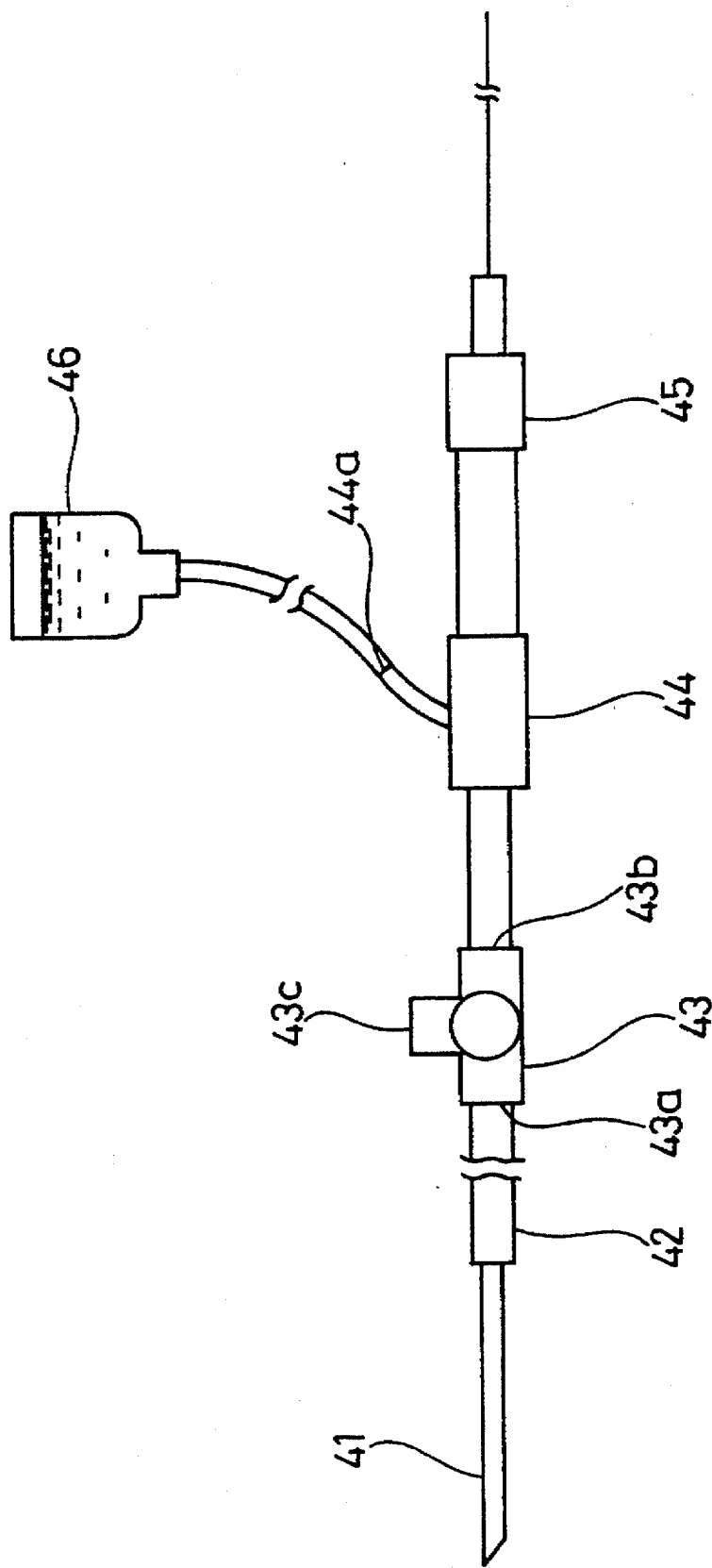
FIG. 3 shows the operation of the sensor 11 indicated in FIG. 2

FIG. 2 gives a detailed diagram of the system put to use. The physiological signal detecting means 1 comprises a plurality of sensors 11 for detecting physiological signals, amplifiers 12 for amplifying the output from the sensors, filters 13 for removing noises from the output of the amplifiers, and A/D converters 14 for A/D converting the output from the filters. In this example, the sensors 11 are all transducers for detecting blood pressures. Normally, blood pressure measurement takes place by means of a catheter inserted into a blood vessel as shown in FIG. 3. Namely, a guide tube 42 is connected at one end with a catheter 41 and at the other end with the first opening 43a of a three-way stopcock 43. The second opening 43b of the stopcock 43 is connected with one end of a flushing device 44 whose other end is connected to a transducer 45. The flushing device 44 has a solution injecting inlet 44a through which, for example, heparinized saline can be introduced from a bottle 46 into the system. When blood pressure is measured, the third opening 43c of the stopcock 43 is closed, and the first opening 43a is connected to the second opening 43b so that heparinized saline may flow little by little through the catheter 41 into blood stream, thereby preventing the counterflow of blood into the catheter 41. In this example, each sensor 11 comprises a catheter 41 inserted into an appropriate vessel for the measurement of arterial pressure, pulmonary arterial pressure or central venous pressure, and a transducer 45 connected thereto through a three-way stopcock 43 and a flushing device 44.

Figure 4:
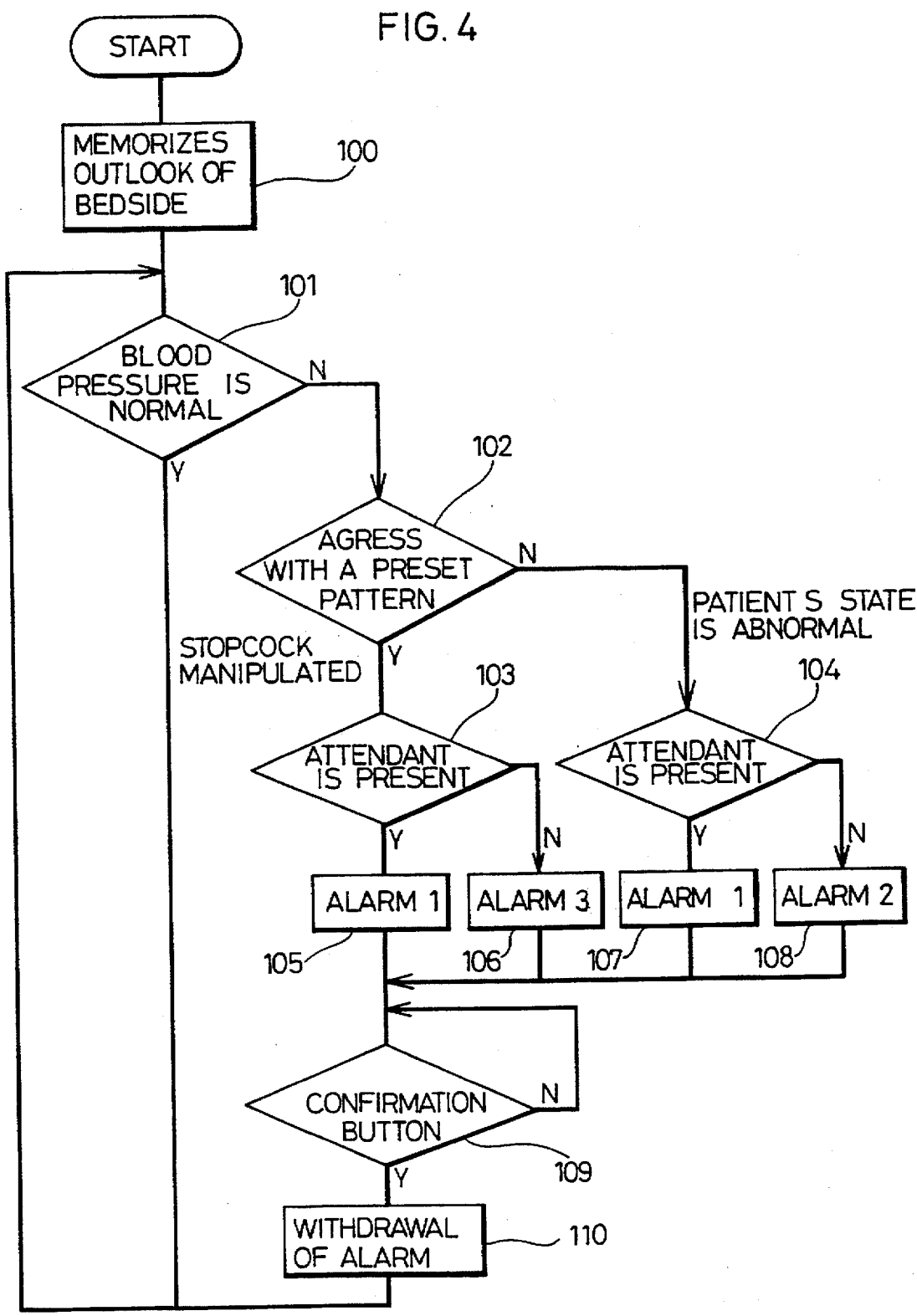
FIG. 4 gives a flow-chart to show the operation of the system indicated in FIG. 2.

Turn to FIG. 2 again. The image detecting means 3 of this system is a videocamera 20. The outputs from the A/D converter 14 and the videocamera 20 are fed through an I/O interface 22 to a state recognizing unit 21. The state recognizing unit 21 is a microcomputer incorporating the I/O interface 22, a CPU 23, a ROM 24 and a RAM 25. The I/O interface 22 acts as a mediator of signals between the state recognizing unit 21 and external devices, and the CPU 23 controls the state recognizing unit 21 and performs programs stored in the ROM 24. FIG. 4 gives a flow-chart of commands underlying the execution of such a program. The RAM 25 is a memory for read/write which is necessary when the CPU 23 is engaged in the processing of information.

In this example, a confirmation button 26 is connected to the I/O interface 22, and when medicare personnel such as a physician or a nurse confirms the reception of an alarm by pressing the button, the signal will be transmitted to the CPU 23.

The state recognizing unit 21 incorporates the first evaluating means 2, the second evaluating means 4 and the alarm type determining means 5 shown in FIG. 1. As will be seen later, the steps 101 and 102 are performed by the first evaluating means 2, the steps 103 and 104 are performed by the second evaluating means 4, and the steps 105 to 108 are performed by the alarm type determining means 5.

The alarm delivery means 6 consists of a display 31, a speaker 32 and a pager system 33, each of which sends an output corresponding with the output of the CPU 23. The display 31 and speaker 32 are placed at the bedside of the patient.

Figure 5:
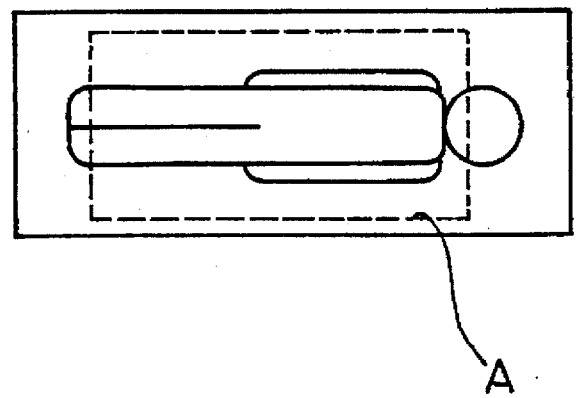
FIG. 5 shows the frame of the bedside image.
Figure 7:
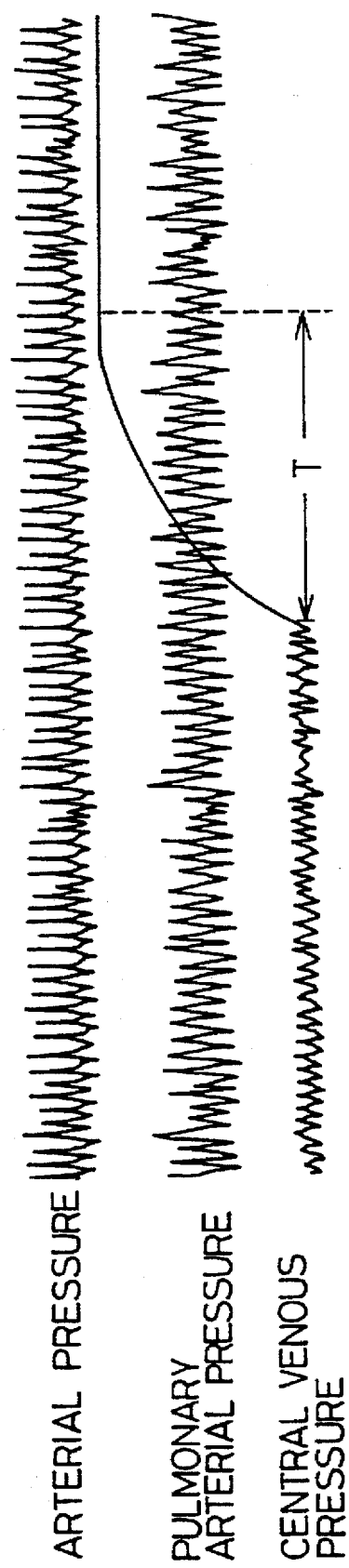
FIG. 7 shows blood pressure data to be measured by the physiological signal detecting means 1 indicated in FIG. 2

The operation of the system having the constitution as described above will be explained below with reference to the flow-chart of FIG. 4. The operator starts the system after having checked that no one except the patient is present at a predetermined area A around the patient's bed such shown in FIG. 5. Thus, at the step 100, the CPU 23 receives from the camera 20 the image data of the predetermined area A around the patient's bed, or the data indicating no one being present around the patient's bed except the patient himself/herself, and memorizes them. Then, the CPU 23 advances to the step 101, receives blood pressure data from the physiological signal detecting means 1 and evaluates whether they are normal or not. The evaluation is achieved depending on whether any one of blood pressures monitored exceeds a predetermined level. If the CPU determines any one of the blood pressures as abnormal, it advances to the step 102 where it starts to evaluate whether the abnormal change with time in blood pressure conforms with a predetermined pattern. One such example is the wave pattern seen during the period of T in the central venous pressure record in FIG. 7. This pattern is typically derived when a physician or a nurse closes the opening 43b of the three-way stopcock 43 depicted in FIG. 3, for example, to extract blood from the patient or to inject a drug into the patient. When the CPU determines a given pattern in the blood pressure data (here in the central venous pressure data in FIG. 7) as correspondent with a predetermined pattern, it advances to the step 103 where it checks whether or not the attendant is present at the bedside. This checking or evaluation takes place by calculating the density correlation of the image data of the current outlook of the bedside with the initial outlook of the bedside. The calculation is made on the basis of the following equation:

[Equation 1]

$$R = \frac{\frac{1}{N^2} \sum_{i=1}^{N} (f_i - \bar{f}) \times (g_i - \bar{g})}{\sqrt{\frac{1}{N^2} \sum_{i=1}^{N} (f_i - \bar{f})^2 \times \frac{1}{N^2} \sum_{i=1}^{N} (g_i - \bar{g})^2}}$$ [Equation 1]

where fi represents the density of a given pixel of the initial image, gi represents the density of a given pixel of the current image, N represents the total number of pixels, f-represents the average density of the initial image, and g- represents the average density of the current image.

Figure 6:
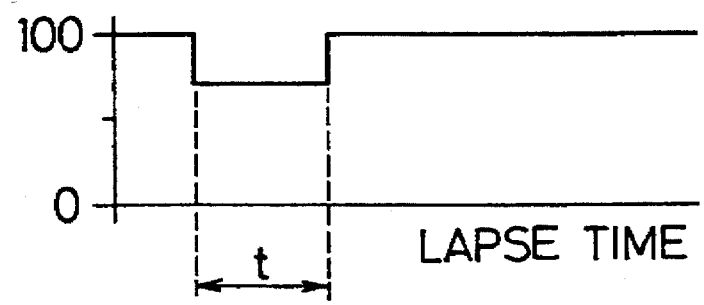
FIG. 6 shows changes in the density correlation of bedside images with time.

The density correlation, as is shown in FIG. 6, will remain about 100% as long as no one is present at the bedside, and become obviously lower than 100% during the period of t when the attendant is around the bedside. Accordingly, when the CPU compares the density correlation of a given moment with a preset level that is definitely lower than 100%, and determines it being lower than that preset level, it concludes that the attendant is around the bedside at that moment. Conversely, when the CPU finds that the density correlation of a given moment is higher than the preset level, it concludes that no one is present around the bedside. The CPU, after concluding at the step 103 that the attendant is around the bedside, advances to the step 105, and gives the alarm 1 signal or a less serious signal to the alarm delivery means 6. Conversely, when the CPU concludes at the step 103 that no one is present around the bedside, it advances to the step 106, and gives the alarm signal 3 or the most serious signal to the alarm delivery means 6. Further, when the CPU determines at the step 102 that the current wave pattern in blood pressure does not agree with the predetermined pattern, it advances to the step 104, and checks, in the same manner as in the step 103, whether anyone is present around the bedside. When the CPU judges someone is around the bedside, it advances to the step 107, and gives the alarm signal 1 or a less serious signal to the alarm delivery means 6. Conversely, when the CPU judges at the step 104 that no one is present around the bedside, it advances to the step 108 and gives the alarm signal 2 or a moderately serious signal to the alarm delivery means 6. The alarm delivery means 6, comprising a display 31, a speaker 32 and a pager system 33, delivers an appropriate alarm according to the alarm signal it has received.

FIG. 8 gives a list of alarm signals, alarm outputs corresponding with those signals, and amounts of stresses those outputs might give to the patient. The visual alarm in the figure is an alarm given visually by the characters on the display 31 which tells that something abnormal happens. The characters, or the meaning and seriousness they convey varies according to the alarm signal. The pager system is activated only when the alarm signal 3 is delivered.

The evaluations made at the steps 101 to 104 in FIG. 4 result in delivery of different alarm signals shown in the steps 105 to 108. FIG. 9 presents in a more simplified manner the relations among causes of abnormalities, presence or absence of the attendant and the seriousness of alarm signals. The step 105 represents the situation where someone is around the bedside and handles the measuring means. In this case abnormalities arise from the disorganized stopcock, or from the measuring means manipulated by medicare personnel for treatment or nursing purposes. Thus, such abnormalities have been thought as less serious, and made to give the alarm 1 signal or a less serious signal.

The step 106 represents the situation where no one is present around the bedside, and the stopcock is disorganized. In this case abnormalities arise from the measuring means due to the movement of the patient. Thus such abnormalities have been thought as most serious, and made to give the alarm 3 signal or the most serious signal.

The step 107 represents the situation where someone is around the bedside, and abnormalities arise in blood pressure data while the stopcock remains intact. In this case abnormalities arise from the patient himself/herself. This situation has been thought, however, not serious because there is someone attending at the bedside, and made to give the alarm 1 signal or a less serious signal.

The step 108 represents the situation where no one is present around the bedside, and abnormalities arise in blood pressure data while the stopcock remains intact. In this case abnormalities arise from the patient himself/herself and there is none to attend him/her. Therefore, the situation has been thought as moderately serious, and made to give the alarm signal 2 or a moderately serious signal.

Then, the CPU 23 advances to the step 109 and checks whether the confirmation button is pressed or not. When it finds the button is pressed, it advances to the step 110, gives a stop signal to the alarm delivery means 6, and returns to the step 101.

FIG. 10 compares types of abnormalities with corresponding alarm signals for a typical situation most commonly encountered at bedside, as an illustration of the operation of this system. In this case, the alarm 3 signal or the most serious signal was delivered when a nurse handled a stopcock to extract a blood sample, forgot to put it into order again, and left the bedside.

According to this system, the alarm delivery means 6 is provided, in addition to the speaker 32, with the display 31 and the pager system 33. Thus, the alarm therefrom can be delivered without fail to the person in attendance. Or the alarm can take any other form as long as it is conveyed without fail to medicare personnel engaged in treatment or nursing.

In the present system the image detecting means uses a videocamera, but it can use an infrared-ray camera or a thermographic camera with the same results.

In the present system the physiological signals consist of blood pressures, but they may include electrocardiological signals or the saturation of oxygen partial pressure.

What is claimed is:

1. A medical alarming system for informing an abnormal event when an abnormality occurs in the output of a physiological signal detecting means for measuring the physiological signal of a patient in a bed, comprising:

a first evaluating means for evaluating whether the current output from the physiological signal detecting means is normal or not;

an image detecting means for detecting the image of the bedside of the patient;

a second evaluating means for evaluating whether the current image of the bedside detected by the image detecting means agrees with a predetermined criterion or not;

an alarm type determining means for determining, for the case judged to be abnormal by the first evaluating means, the alarm type according to the judgement given by the second evaluating means for the same case; and an alarm delivering means for delivering the type of alarm that has been determined by the alarm type determining means;

and wherein the first evaluating means includes at least one sensor, the first evaluating means, when it evaluates an event as abnormal, evaluates further whether the abnormality comes from the sensor or from the patient; and the alarm type determining means determines, for the case judged to be abnormal by the first evaluating means, the alarm type according to the judgement of the type of the abnormality given by the first evaluating means and to the judgement given by the second evaluating means.

2. The medical alarming system as described in claim 1 wherein the second evaluating means evaluates whether the current image of the bedside agrees with a predetermined criterion according to the presence/absence of a human image.

3. A medical alarming system for informing an abnormal event when an abnormality occurs in the output of a physiological signal detecting means for measuring the physiological signal of a patient in a bed, comprising:

a first evaluating means for evaluating whether the current output from the physiological signal detecting means is normal or not;

an image detecting means for detecting the image of the bedside of the patient;

a second evaluating means for evaluating whether the current image of the bedside detected by the image detecting means agrees with a predetermined criterion or not;

an alarm type determining means for determining, for the case judged to be abnormal by the first evaluating means, the alarm type according to the judgement given by the second evaluating means for the same case; and an alarm delivering means for delivering the type of alarm that has been determined by the alarm type determining means;

the alarm type determining means determines, for the case judged to be abnormal by the first evaluating means, the alarm type by further evaluating the seriousness of the alarm according to the judgement given by the second evaluating means; and the alarm delivering means delivers such type of alarm that the less the seriousness is evaluated, the less the stress is given to the patient.

4. A medical alarming system for informing an abnormal event when an abnormality occurs in the output of a physiological signal detecting means for measuring the physiological signal of a patient in a bed, comprising:

a first evaluating means for evaluating whether the current output from the physiological signal detecting means is normal or not;

an image detecting means for detecting the image of the bedside of the patient;

a second evaluating means for valuating whether the current image of the bedside detected by the image detecting means agrees with a predetermined criterion or not;

an alarm type determining means for determining, for the case judged to be abnormal by the first; evaluating means, the alarm type according to the judgement given by the second evaluating means for same case; and an alarm delivering means for delivering the type of alarm that has been determined by the alarm type determining means;

and wherein the first evaluating means includes at least one sensor, the first evaluating means, when it evaluates an event as abnormal, evaluates further whether the abnormality comes from the sensor or from the patient;

the second evaluating means evaluates whether the current image of the bedside agrees with a predetermined criterion according to the presence/absence of a human image;

the alarm type determining means determines, for the case judged to be abnormal by the first evaluating means, the alarm type according to the judgement of the type of the abnormality given by the first evaluating means and to the judgement given by the second evaluating means;

the alarm delivering means delivers such type of alarm that the less the seriousness is evaluated, the less the stress is given to the patient; and further the alarm type determining means evaluates as most serious the situation where no human image is present, and the abnormality comes from the sensor, as moderately serious the situation where no human image is present, and the abnormality comes from the patient, and as less serious the situation where a human image is present and the abnormality comes from the sensor and, in addition, the situation where a human image is present and the abnormality comes from the patient.

* * * * *

UNITED STATES PATENT AND TRADEMARK OFFICE
CERTIFICATE OF CORRECTION

PATENT NO. : 5,696,492

DATED : December 9, 1997

INVENTOR(S) : Takanori Sakamaki; Yasuhiro Fukui; and Hajime Ysuda

It is certified that error appears in the above-identified patent and that said Letters Patent is hereby corrected as shown below:

Column 7,

Claim 4, line 10, "a second evaluating means for valuating" should be --a second evaluating means for evaluating--.

Signed and Sealed this

Third Day of March, 1998

Attest:

BRUCE LEHMAN

*Attesting Officer*    *Commissioner of Patents and Trademarks*